United States Patent
Seakins et al.

(10) Patent No.: US 6,895,803 B2
(45) Date of Patent: May 24, 2005

(54) HUMIDITY SENSOR

(75) Inventors: Paul John Seakins, Auckland (NZ); Malcolm David Smith, Auckland (NZ); Kaumali Prasangika Abeysinghe, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 0 days.

(21) Appl. No.: 09/974,226

(22) Filed: Oct. 10, 2001

(65) Prior Publication Data

US 2002/0078733 A1 Jun. 27, 2002

(30) Foreign Application Priority Data

Oct. 20, 2000 (NZ) ................................. 507682

(51) Int. Cl.[7] ............................................. G01N 19/10
(52) U.S. Cl. .................... 73/29.02; 73/29.02; 73/29.01; 73/23.2; 73/335.02; 73/335.05
(58) Field of Search ............................. 73/29.02, 29.01, 73/23.2, 335.02, 335.05

(56) References Cited

U.S. PATENT DOCUMENTS

| | | | |
|---|---|---|---|
| 4,143,177 A | | 3/1979 | Kovac et al. |
| 5,777,206 A | | 7/1998 | Zuchner et al. |
| 5,792,938 A | * | 8/1998 | Gokhfeld ................... 73/29.02 |
| 6,039,696 A | * | 3/2000 | Bell ....................... 128/204.21 |
| 6,349,722 B1 | * | 2/2002 | Gradon et al. ......... 128/203.17 |

* cited by examiner

Primary Examiner—Hezron Williams
Assistant Examiner—André K. Jackson
(74) Attorney, Agent, or Firm—Trexler, Bushnell, Giangiorgi, Blackstone & Marr, Ltd.

(57) ABSTRACT

A method and apparatus are described for sensing the absolute humidity of gases where the relative humidity of gases are measured, the humidity transducer is heated, the resulting temperature measured and the absolute humidity calculated (based on the power to heat said transducer, the temperature of said transducer and the relative humidity).

In further embodiments the humidity transducer may be heated to a pasteurisation temperature, to substantially kill any common pathogens present on the humidity transducer. The flow rate may be determined to estimate a more instantaneous valve of humidity. The operation of the sensor may be continually monitored for correct operation and various constructions disclosed for improving the efficiency of operation.

20 Claims, 2 Drawing Sheets

HUMIDITY SENSOR

FIELD OF THE INVENTION

The present invention relates to the use of heated humidity sensors particularly though not solely to the use of heated humidity sensors with respiratory humidifiers for assisted patient breathing.

BACKGROUND OF THE INVENTION

Heated humidity sensors are hereby described that allow the measurement of humidity in gases having a dewpoint above the temperature of the surrounding environment. Problems associated with such gas streams include lack of sensor accuracy at high relative humidity and the possibility of liquid condensate flowing onto the sensor. A further disadvantage of measurement in high dewpoint gases is the possibility of sensor failure or misreading.

Such humidity sensors could be used, for example, as part of a humidity-controlled medical humidifier. This introduces design constraints such as small size, robustness and ability to be sterilised to prevent cross-contamination between patients.

When a medical humidifier is used with a respiratory ventilator, gas flow and absolute humidity can change rapidly in a cyclic manner. These changes typically happen faster than the response time of the humidity sensor, which gives a "time average" of the humidity surrounding it. This means that certain key humidity parameters, such as average absolute humidity during the inspiratory part of the flow cycle, are unable to be measured.

In U.S. Pat. No. 4,143,177 capacitive-type humidity sensor is described, as well as how a heater and temperature sensor can be incorporated into the humidity sensor to allow stable temperature control of the humidity sensor at temperatures above that of the surrounding gas. This enables the humidity sensor to avoid condensation in gases of high humidity. The heater can be manufactured around or underneath the humidity sensor. It also describes how the heater element can be simultaneously used to measure temperature, i.e. the heater element and temperature sensor are combined in one element. This makes sensor construction easier.

U.S. Pat. No. 5,777,206 also describes a heated capacitive-type humidity sensor. A single resistor is used in this patent both as a heater and a temperature sensor, for controlling the humidity sensor temperature above the gas temperature. U.S. Pat. No. 5,777,206 also describes calculating the absolute or relative humidity from knowledge of the temperature of the sensor. Further disclosure includes a method for determining the gas flow rate based on the amount of heat being supplied to the heated capacitive sensor to determine the gas flow rate past the sensor. Whereas U.S. Pat. No. 5,777,206 uses a resistor to provide sensor heating and temperature measurement, U.S. Pat. No. 4,143,177 uses a P-N semiconductor diode junction to provide the same functions.

SUMMARY OF THE INVENTION

It is therefore an object of the present invention to provide a heated humidity sensor which goes some way to overcoming the abovementioned disadvantages in the prior art or which will at least provide the industry with a useful choice.

Accordingly in a first aspect the present invention consists in a system for automatically disinfecting an absolute humidity sensing apparatus for sensing the absolute humidity of respiratory gases comprising:

a humidity transducer providing a first signal, said first signal indicative of the relative humidity of said gases, a heater associated with or in substantial thermal contact with said humidity transducer and adapted to heat at least a portion of said humidity transducer depending on energisation power supplied thereto, a temperature sensor associated with or in substantial thermal contact with said humidity transducer and providing a second signal, said second signal indicative of the temperature of said humidity transducer, and a controller or processor configured to operate in at least two modes, a first absolute humidity measurement mode configured to provide a first said energisation power to said heater to heat said humidity transducer to an operating temperature and receives said first signal and said second signal and calculates an estimate of the absolute humidity of said gases based thereon, and a second disinfection mode configured to provide a second said energisation power to said heater to heat said humidity transducer to a predetermined disinfection temperature, said disinfection temperate being higher than said operating temperature and adequate to substantially kill the majority of any common pathogens present on said humidity transducer.

In a second aspect the present invention consists in a system for interpolating the output of an absolute humidity sensing apparatus for sensing the absolute humidity of a respiratory flow of gases composing:

a humidity transducer providing a first signal, said first signal indicative of the relative humidity of said flow of gases, a heater associated with or in substantial thermal contact with said humidity transducer and adapted to heat at least a portion of said humidity transducer depending on energisation power supplied thereto, a temperature sensor associated with or in substantial thermal contact with said humidity transducer and providing a second signal, said second signal indicative of the temperature of said humidity transducer, a flow sensor configured to in use provide an indication of the flow rate of said gases and having a response time significantly lower than said humidity sensor or said temperature sensor, and, a controller or processor configured to:

(i) provide a first said energisation power to said heater to heat said humidity transducer to an operating temperature;

(ii) receive said first signal and said second signal;

(iii) calculate an estimate of the absolute humidity of said flow of gases based on said first signal and said second signal;

(iv) store information on said absolute humidity over a period of time;

(v) sense the flow rate of said flow of gases;

(vi) store information on said flow rate of said gases over said period of time in said storage means; and (vii) interpolate humidity values for said flow of gases during a portion of said period of time based on said stored flow rate of gases during said portion and said stored absolute humidity during said portion.

In a third aspect the invention may broadly be said to consist in a system for testing the accuracy of an absolute humidity sensing apparatus for sensing the absolute humidity of respiratory gases comprising:

a humidity transducer providing a first signal, said first signal indicative of the relative humidity of said gases, a heater associated with or in substantial thermal contact with said humidity transducer and adapted to heat at least a portion of said humidity transducer depending on energisation power supplied thereto, a temperature sensor associated with or in substantial thermal contact with said humidity transducer and providing a second signal, said second signal indicative of the temperature of said humidity transducer, and a controller or processor adapted to provide energisation power to said heater to heat said humidity transducer to at least two calibration temperatures and receive said first signal and said second signal and calculate an estimate of the absolute humidity of said gases based thereon, and detect or determine whether the apparatus is operating correctly, based on whether said absolute humidity is consistent over said temperatures.

In a fourth aspect the present invention to consists in a system for locating an absolute humidity sensor within a gases delivery apparatus for supplying a flow of respiratory gases to a patient comprising:

a gases supply adapted to provide a flow of gases at a desired pressure, a humidifier having and inlet and an outlet, said inlet adapted to be in fluid communication wit said gases supply said humidifier thereby providing water vapour to humidify said flow of gases as they pass through said humidifier, a conduit in use adapted to be connected to said outlet and accepting said flow of gases therefrom, said conduit including an interior and an exterior, said conduit in use conveying said flow of gases through said interior, configured such that in use a portion of said conduit adjacent said outlet being substantially vertical and including a protrusion located in the interior of said substantially vertical portion, and a humidity sensor adapted to be located in said interior providing an estimate of the absolute humidity of said flow of gases, in use said humidity sensor juxtapositioned below said protrusion, said protrusion thereby substantially preventing any liquid water from flowing down said conduit onto said humidity sensor.

In a fifth aspect the present invention to consists in a method of automatically disinfecting an absolute humidity sensor for respiratory gases comprising the steps:

operating in an absolute humidity measurement mode comprising the steps using a humidity transducer to sense the relative humidity of said gases, heating at least a portion of said humidity transducer and sensing the temperature of said humidity transducer, and calculating an estimate of the absolute humidity of said gases based said temperature of said transducer and said relative humidity, operating in a disinfecting mode comprising the steps heating said humidity transducer to a predetermined disinfection temperate, said disinfection temperature being adequate to substantially kill the majority of any common pathogens present on said humidity transducer.

In a sixth aspect the present invention to consists in a method of interpolating the output of an absolute humidity sensor for respiratory gases comprising the steps:

using a humidity sensor to sense the relative humidity of said gases, heating at least a portion of said humidity sensor to an operating temperature, calculating an estimate of the absolute humidity of said flow of gases based on said relative humidity and said temperature, storing information on said absolute humidity over a period of time, sensing the flow rate of said flow of gases, said flow rate having a response time significantly lower than said humidity, storing information on said flow rate of said gases over said period of time, and interpolating absolute humidity values for said flow of gases during a portion of said period of time based on said stored flow rate of gases during said portion said stored absolute humidity during said period.

In a seventh aspect the present invention consists in a method of automatically testing the accuracy of an absolute humidity sensor for respiratory gases comprising the steps:

heating at least a portion of said humidity sensor to at least two calibration temperatures, using a humidity sensor to sense the relative humidity of said gases at each temperature, calculating an estimate of the absolute humidity of said gases based on said relative humidity, and said temperature, detection or determining whether the apparatus is operating correctly, based on whether said absolute humidity is substantially consistent over said temperatures.

In a eighth aspect the present invention consists in a method of locating an absolute humidity sensor for respiratory gases comprising the steps:

providing a flow of gases at a desired pressure, humidifying said flow of gases, conveying said flow of gases through the said interior of a conduit and providing at least a portion of said conduit substantially vertical with a protrusion in said interior of said substantially vertical portion, positioning a humidity sensor below said protrusion, said protrusion thereby substantially preventing any liquid water from flowing down said interior onto said humidity sensor, and providing an estimate of the absolute humidity of said flow of gases, based at least from the output of said humidity sensor.

To those skilled in the art to which the invention relates, many changes in construction and widely differing embodiments and applications of the invention will suggest themselves without departing from the scope of the invention as defined in the appended claims. The disclosures and the descriptions herein are purely illustrative and are not intended to be in any sense limiting.

The invention consists in the foregoing and also envisages constructions of which the following gives examples.

BRIEF DESCRIPTION OF THE DRAWINGS

One preferred form of the present invention will now be described with reference to the accompanying drawings in which.

DESCRIPTION OF THE PREFERRED EMBODIMENTS

Figure 1:
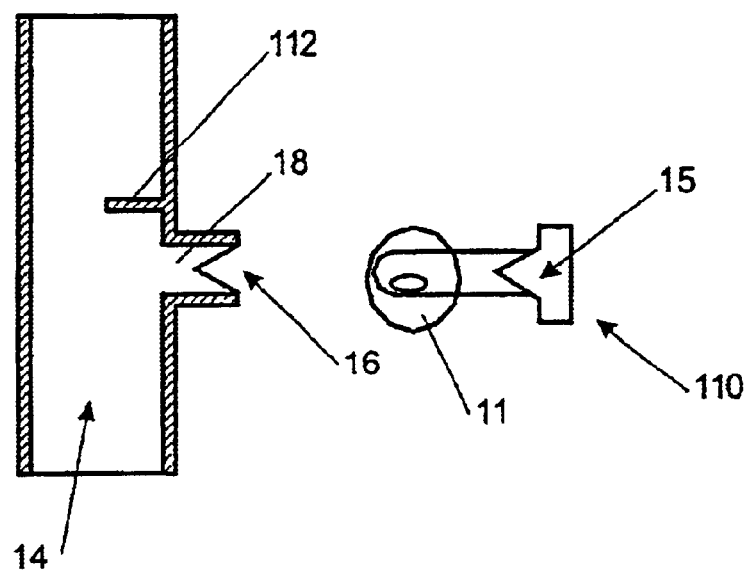
FIG. 1 is a cutaway view of the conduit according to the preferred embodiment of the present invention in use.
Figure 2:
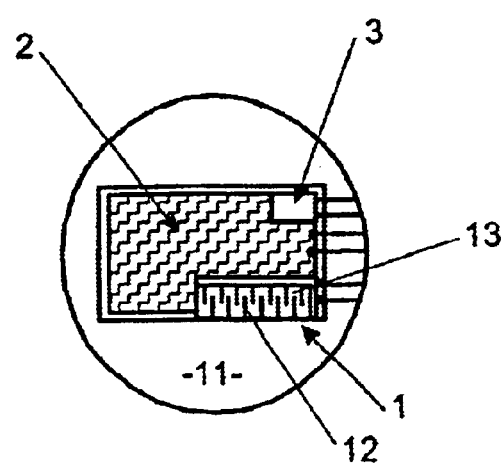
FIG. 2 is a close up side view of the humidity sensor according to the preferred embodiment of the present invention.

The present invention relates to a humidity sensor which is designed:

1. To operate in high dewpoint situations where the relative humidity may be high, and liquid water may be present.
2. To detect sensor misreading or failure.
3. To be strong, robust and capable of sterilisation.
4. When flow is rapidly changing in a cyclic manner, to detect key parameters of the instantaneous absolute humidity waveform by mathematically combining the reading from the humidity sensor with knowledge of the gas flow waveform.

Polymer absorption sensors are well known in the prior art and consist of two parts: a water-vapour porous polymer matrix, and a set of electrical sensing electrodes. The amount of water vapour which is absorbed into the polymer matrix is determined by the relative humidity of the gas in close contact with the polymer matrix. The electrodes allow the measurement of electrical properties related to the amount of water vapour in the polymer matrix. Usually capacitance of the electrodes is measured, as the permittivity of the matrix changes with water content. Alternatively electrical resistance or impedance can be measured.

The invention as shown consists of a relative humidity sensor 1, which is mounted in close thermal contact with a heater 2 and a separate temperature sensor 3 to form assembly 11. Measurement circuit 4 is connected to the humidity sensor 1 and gives an output in relative humidity 5. An adjustable power supply 6 is connected to the heater 2. Measurement circuitry 7 is connected to temperature sensor 3 to give a temperature signal 8 at its output. Control system 9 takes the temperature signal 8 and generates a control signal 10 so that temperature signal 8 remains constant at the desired temperature. In this way all of the elements of assembly 11 are kept at a constant temperature. The relative humidity sensor 1 is preferably of the polymer absorption type. Preferably the sensing mechanism measures capacitance of the polymer matrix 13 using the electrodes 12, although it could alternatively use resistance or impedance measurements of the polymer matrix.

Absolute humidity of a gas can be calculated if the relative humidity and temperature are both known. This calculation is based on well-known physical principles. Due to its mode of operation, the polymer sensor measures the relative humidity of the measured gas at the temperature of the polymer mix 13. Therefore absolute humidity of the gas can be calculated from the relative humidity measured by sensor 1 and the temperature of sensor 1 as measured by temperature sensor 3.

If the polymer matrix is heated by applying heat to heater 2 the measured relative humidity will decrease, however the calculated absolute humidity will remain constant because the absolute humidity of the gas has not changed. Although we still get the same absolute humidity reading from the sensor, there are several advantages that come from heating the sensor. Firstly, formation of condensate on the sensor can be prevented. Secondly, we can measure humidity of gas with a dewpoint above the temperature of the surrounding environment. Lastly, by keeping the sensor at a high temperature we are running it in the low relative humidity region where most sensors are more accurate and linear.

Such a sensor can be used for measuring absolute humidity of any gases. However preferably the sensor is to be used for measuring medical gases. Preferably the medical gases are also respiratory gases, such as are found in a patient breathing circuit. A breathing circuit can be used to connect a patient to either a source of flowing gases, or to a respiratory ventilator.

Preferably the sensor is heated above the temperature of the gas to be measured, although it may be heated to any desired temperature. Preferably the temperature sensor 3 and heater 2 are separate components that are both thermally linked by being part of assembly 11. U.S. Pat. Nos. 4,143,177 and 5,777,206 both describe systems where the temperature sensing and heating functions are combined in a single component.

Since there will be times when the sensing assembly 11 will be in an environment containing liquid water while the heater is off, it is essential that humidity sensor 1 be a water resistant sensor. Such sensors have only recently become available. Such a sensor will recover quickly from contact with liquid water, and this will have no lasting effects on the humidity calibration.

The sensor as described may be mounted in several different ways. In one embodiment a probe 110 could be inserted into a hole 18 in a tube 109 to measure the humidity of the gas inside 14, as shown in FIG. 1. An alternative arrangement would be as a sensor permanently mounted inside a tube. With either arrangement it may be desirable to orient the sensing element in a particular direction in the tube. For instance, a horizontally facing sensing element 1 will cause liquid water on the sensor assembly 11 to run off the probe rather than onto the sensing element. To allow positive location of a probe type sensor in a tube, a key 15 and keyway 16 can be used, as shown in FIG. 1.

Figure 3:
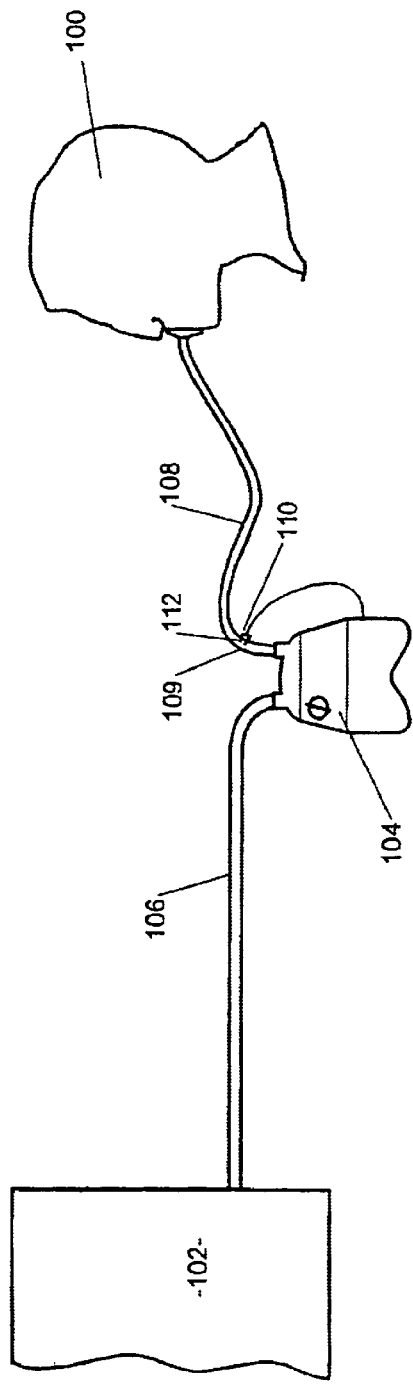
FIG. 3 is a diagram of a system for delivering humidified gases to a patient according to the preferred embodiment of the present invention.
Figure 4:
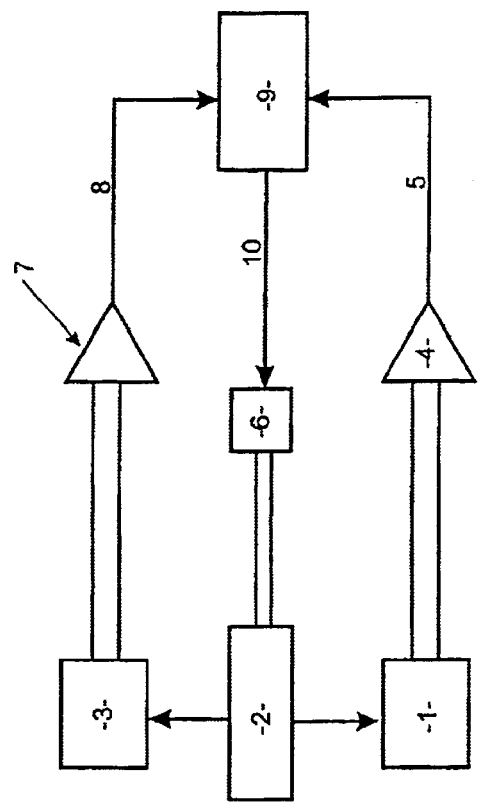
FIG. 4 is a block diagram of the control system according to the preferred embodiment of the present invention.

There are other ways of preventing liquid water from running onto the humidity probe and affecting the humidity reading. For example consider the apparatus shown in FIG. 3. A respiratory system for delivering humidified gases to a patient 100 is shown, including a gases supply 102, a humidifier 104, a conduit 106 connecting the gases supply 102 to the humidifier 104, and a conduit 108 connecting the humidifier 104 to the patient 100. In the configuration shown in FIG. 3 it is seen that the conduit 109 conveying air flow from the humidifier 104 is substantially vertical in the section 109 immediately adjacent the humidifier 104. In the preferred embodiment of the present invention the humidity sensor 110 would be located in this vertical section 109. In this fashion any liquids that were to condense in this vertical section 109 would likely flow down the sides of the conduit 108, some of which would then end up on the humidity sensor 110. In order to prevent this happening a protruding lip 112 in the conduit 108 located above the humidity sensor 110 can be used to deflect liquid water to flow around the sensing assembly.

In a medical environment it is important to be able to sterilise the humidity sensor. Traditional methods such as autoclaving can be very harsh on a humidity sensor. Preferably the sensor assembly 11 would be able to survive autoclaving using steam at 136° C. Other common methods of sterilising a probe are to immerse the probe in a disinfectant. Preferably the sensor assembly 11 would survive this treatment.

Another way of sterilising the heated humidity sensor would be to heat it above the pasteurisation temperature of common pathogens (bacteria and viruses). The hardiest bacteria, Legionella, can be killed by temperatures of 60° C. Preferably the temperature of the sensor is high enough that it kills common pathogens. Alternatively the temperature of the sensor is raised to a high temperature at turn-on to kill pathogens. Alternatively the sensor is periodically heated to a high temperature to kill pathogens.

Another less desirable way of preventing cross-contamination between patients caused by the sensing assembly 11 is to enclose it in a vapour permeable membrane which does not allow the passage of pathogens. For a humidity sensor probe, the semi permeable membrane could be a cap which fits over the probe and attaches to the probe, or alternatively it could be attached to the hole in the tube which the humidity probe fits into.

A further way to reduce the potential of cross-contamination would be to construct the sensor assembly out of bactericidal plastic.

When a humidity sensor is used as part of a humidity control system it is important to be able to detect whether the humidity sensor is functioning correctly or not. This is particularly important if the humidity sensor is used to control a medical humidifier, because excessive levels of absolute humidity can result in patient burns and inadequate levels can cause drying of bodily tissues.

There are several ways of detecting whether the described sensing assemblies are giving incorrect readings. One way is to remove or reduce the power being supplied to heater 2 to drop the temperature of assembly 11. When the relative humidity reaches 100% we should have reached the dewpoint temperature of the gas, and this can be measured using temperature sensor 3. If the absolute humidity corresponding to this dewpoint is substantially different from the absolute humidity measured by the sensor in normal operation then the sensor is faulty.

If water has covered the surface of sensor 1 then the sensor will read 100% relative humidity. If 100% relative humidity is measured, the amount of heating being supplied to heater 2 can be increased so that the temperature of assembly 11 increases. If the 100% relative humidity reading remains after the sensor has been heated to a sufficiently high temperature, then the sensor can be judged to be faulty (or covered in water).

If the sensor is found to be faulty then the power to heater 2 can be discontinued, and the temperature sensor 3 used to give an estimate of the dewpoint of the gas. This can be converted to an absolute humidity figure assuming 100% relative humidity. The true absolute humidity will only be equal or less than the estimated absolute humidity, so this method provides an upper limit on the humidity control to prevent patient burns.

When a medical humidifier is used with a respiratory ventilator, flow rate and absolute humidity of the gas 14 can change rapidly in a cyclic manner. These changes typically happen faster than the response time of the humidity sensor 1, which gives a "time average" of the humidity surrounding it. However in these situations it is often desirable to know certain parameters such as the peak level of humidity or the average humidity during the inspiratory part of the flow cycle.

If certain parameters related to the flow rate are known, either through instantaneous flow measurement or through knowledge of other flow parameters, it is possible to mathematically combine this knowledge with the reading from the humidity sensor. This allows estimation of certain key humidity parameters, such as average absolute humidity during the inspiratory part of the flow cycle. The algorithm required could use an equation to estimate the value of the required parameter, or it could use a look up table.

Flow can be measured directly using a flow rate sensor, e.g. by measuring heat loss from a heated body. The heated humidity sensor as described is such a heated body, and the amount of power required to keep the sensor assembly at a particular temperature will give an indication of the gas rate. Alternatively a separate flow sensor could be used, or this information may be obtained electronically from the ventilator.

What is claim is:

1. A system for automatically disinfecting an absolute humidity sensing apparatus for sensing the absolute humidity of respiratory gas comprising:
   a humidity transducer providing a first signal, said first signal indicative of the relative humidity of said gas,
   a heater associated with or in substantial thermal contact with said humidity transducer and adapted to heat at least a portion of said humidity transducer depending on energisation power supplied thereto,
   a temperature sensor associated with or in substantial thermal contact with said humidity transducer and providing a second signal, said second signal indicative of the temperature of said humidity transducer, and
   a controller or processor configured to operate in at least two modes, a first absolute humidity measurement mode configured to provide a first energisation power to said heater to heat said humidity transducer to an operating temperature and receives said first signal and said second signal and calculates an estimate of the absolute humidity of said gas based thereon, and a second disinfection mode configured to provide a second energisation power to said heater to heat said humidity transducer to a predetermined disinfection temperature, said disinfection temperature being higher than said operating temperature and adequate to substantially kill the majority of any common pathogens present on said humidity transducer.

2. A system as claimed in claim 1 wherein said disinfection temperature is above 60° C.

3. A system as claimed in claim 1 or 2 wherein said operating temperature is above the temperature of said gas.

4. A system for interpolating the output of an absolute humidity sensing apparatus for sensing the absolute humidity of a flow of respiratory gas comprising:
   a humidity transducer providing a first signal, said first signal indicative of the relative humidity of said flow of gas;
   a heater associated with or in substantial thermal contact with said humidity transducer and adapted to heat at least a portion of said humidity transducer depending on energisation power supplied thereto;
   a temperature sensor associated with or in substantial thermal contact with said humidity transducer and providing a second signal, said second signal indicative of the temperature of said humidity transducer
   a flow sensor configured in use to provide an indication of the flow rate of said gas and having a response tune significantly lower than said humidity transducer or said temperature sensor, and;
   a controller or processor configured to:
   (i) provide a first said energisation power to said heater to heat said humidity transducer to an operating temperature;
   (ii) receive said first signal and said second signal;
   (iii) calculate an estimate of the absolute humidity of said flow of gas based on said first signal and/or said second signal;
   (iv) store information on said absolute humidity over a period of time;
   (v) sense the flow rate of said flow of gas;
   (vi) store information on said flow rate of said gas over said period of time; and (vii) interpolate absolute humidity values for said flow of gas during a portion of said period of time based on said stored flow rate of gas during said portion of said period of time and said stored absolute humidity during said portion of said period of time.

5. A system as claimed in claim 4 wherein said period of time at least relates to one breathing cycle of a patient receiving respiratory therapy using said flow of gas.

6. A system as claimed in claim 5 wherein said portion of said period of time relates to the inspiratory phase of said patient's breathing cycle.

7. A system for automatically testing the accuracy of an absolute humidity sensing apparatus for sensing the absolute humidity of respiratory gas comprising:
   a humidity transducer providing a first signal, said first signal indicative of the relative humidity of said gas,
   a heater associated with or in substantial thermal contact with said humidity transducer and adapted to heat at least a portion of said humidity transducer depending on energisation power supplied thereto,
   a temperature sensor associated with or in substantial thermal contact with said humidity transducer and providing a second signal, said second signal indicative of the temperature of said humidity transducer, and
   a controller or processor configured to provide energisation power to said heater to heat said humidity transducer to at least two different calibration temperatures, receive said first signal and said second signal and calculate an estimate of the absolute humidity of said gas at each different calibration temperature based thereon, and detect or determine whether the apparatus is operating correctly, based on whether said absolute humidity is consistent over said temperatures.

8. A system as claimed in claim 7 wherein said correct operation of said apparatus at least relates to whether said estimate of the absolute humidity of said gas is accurate within predetermined limits.

9. A system as claimed in claim 8 wherein said accuracy of said absolute humidity is monitored in at least one aspect by detecting the presence of liquid water on said humidity transducer.

10. A system as claimed in 9 wherein said detection of liquid water comprises the steps:
   a) storing absolute humidity values during normal operation;
   b) providing a third said energisation power to said heater to heat said humidity transducer to the dewpoint of said gas (where the relative humidity just reaches 100%);
   c) comparing the absolute humidity reading at dew point with that during normal operating (stored in step (a)); and if there is a substantial difference providing a fourth signal indicative of incorrect or faulty operation.

11. A system as claimed in 9 wherein said detection of liquid water comprises the steps of:
   a) determining whether said first signal indicates 100% relative humidity,
   b) providing a fourth said energisation power to said heater to heat said humidity transducer to a substantially higher temperature;
   c) if the relative humidity does not reduce from 100% providing a fourth signal indicative of incorrect or faulty operation.

12. A system as claimed in claim 10 or 11 wherein if said fourth signal indicates incorrect or faulty operation said controller or processor provides a fifth said energisation power to said heater to heat said humidity transducer to substantially evaporate said liquid water therefrom.

13. A system as claimed in claim 10 or 11 wherein, if said fourth signal indicates incorrect or faulty operation said controller or processor discontinuing said energisation power to said heater, and using said second signal to estimate an upper limit for the absolute humidity of said flow of gas.

14. A system for locating an absolute humidity sensor within a gas delivery apparatus for suppling a flow of respiratory gas to a patient comprising:
   a gas supply adapted to provide a flow of gas at a desired pressure,
   a humidifier having an inlet and an outlet, said inlet adapted to be in fluid communication with said gas supply and said humidifier thereby providing water vapour to humidify said flow of gas as they pass through said humidifier,
   a conduit in use adapted to be connected to said outlet and accepting said flow of gas there from, said conduit including an interior and an exterior, said conduit in use conveying said flow of gas through said interior, in use a portion of said conduit adjacent said outlet being substantially vertical and including a protrusion within the interior of said substantially vertical portion, and
   a humidity sensor adapted to be located in said interior providing an estimate of the absolute humidity of said flow of gas, said humidity sensor juxtapositioned below said protrusion, said protrusion thereby substantially preventing any liquid water from flowing down said conduit onto said humidity sensor.

15. A system as claimed in claim 14 wherein said gas conduit having an aperture including a keyway, said humidity sensor comprising a humidity transducer provided in a sensor housing, said housing adapted to engage with said aperture and having a key which engages with said keyway in said aperture such that said housing can only be installed in said aperture in a single orientation.

16. A system as claimed in claim 14 wherein said humidity sensor is permanently housed within said conduit.

17. A method of automatically disinfecting an absolute humidity sensor for respiratory gas comprising the steps:
   operating in an absolute humidity measurement mode comprising the steps of
   using a humidity transducer to sense the relative humidity of said gas;
   heating at least a portion of said humidity transducer to an operating temperature and sensing the temperature of said humidity transducer, and
   determining an estimate of the absolute humidity of said gas based on said temperature and said relative humidity;
   operating in a disinfecting mode comprising the step of
   heating said humidity transducer to a predetermined disinfection temperature, said disinfection temperature being higher than said operating temperature and adequate to substantially kill the majority of any common pathogens present on said humidity transducer.

18. A method of interpolating the output of an absolute humidity sensor of respiratory gas comprising the steps:
   using a humidity sensor to sense the relative humidity of said gas,
   heating at least a portion of said humidity sensor to an operating temperature,
   determining an estimate of the absolute humidity of said flow of gas based on said relative humidity and temperature, said absolute humidity determination having a response time, storing said relative or absolute humidity over a period of time, sensing the flow rate of said gas, said flow rate having a response time significantly lower than said humidity, storing said flow rate over said period of time, and interpolating values for absolute humidity during a portion of said period of time based on said stored flow rate and said stored absolute humidity.

19. A method of automatically testing the accuracy of an absolute humidity sensor for respiratory gas comprising the steps:

using a humidity sensor to sense the relative humidity of said gas at each temperature, heating at least a portion of said humidity sensor to at least two different calibration temperatures, calculating an estimate of the absolute humidity of said gas at each temperature based on said relative humidities and said temperatures, detecting or determining whether the apparatus is operating correctly, based on whether said absolute humidity is substantially consistent over said temperatures.

20. A method of locating an absolute humidity sensor for respiratory gas comprising the steps:

providing a flow of gas at a desired pressure, humidifying said flow of gas, conveying said flow of gas through the said interior of a conduit and providing at least a portion of said conduit substantially vertical with a protrusion in said interior of said substantially vertical portion, positioning a humidity sensor within the flow of gas below said protrusion, said protrusion thereby substantially preventing any liquid water from flowing down said interior onto said humidity sensor, and providing an estimate of the absolute humidity of said flow of gas, based on the temperature and relative humidity of said gas from said humidity sensor.

* * * * *